(12) United States Patent
Mitchell

(10) Patent No.: US 7,153,296 B2
(45) Date of Patent: Dec. 26, 2006

(54) RELEASABLE TUBING CONNECTOR

(76) Inventor: Martin S. Mitchell, 1020 NE. 27th Ave., Pompano Beach, FL (US) 33062

( * ) Notice: Subject to any disclaimer, the term of this patent is extended or adjusted under 35 U.S.C. 154(b) by 430 days.

(21) Appl. No.: 10/702,723

(22) Filed: Nov. 7, 2003

(65) Prior Publication Data

US 2005/0101939 A1    May 12, 2005

(51) Int. Cl.
*A61M 25/16* (2006.01)
*A61M 25/18* (2006.01)
*A61M 39/00* (2006.01)
*A61M 39/10* (2006.01)

(52) U.S. Cl. .................... 604/533; 604/905; 251/149.9

(58) Field of Classification Search ................ 604/246, 604/249, 256, 533–535, 538–539, 905; 251/149.3, 251/149.6, 149.7, 149.9
See application file for complete search history.

(56) References Cited

U.S. PATENT DOCUMENTS

| 2,795,438 | A |   | 6/1957  | Oetiker |
|-----------|---|---|---------|---------|
| 3,674,050 | A |   | 7/1972  | Kuffer et al. |
| 3,858,910 | A |   | 1/1975  | Oetiker |
| 4,436,125 | A | * | 3/1984  | Blenkush ..................... 141/330 |
| 4,541,457 | A | * | 9/1985  | Blenkush ............... 137/614.06 |
| 5,033,777 | A | * | 7/1991  | Blenkush ..................... 285/317 |
| 5,492,147 | A |   | 2/1996  | Challender et al. |
| 5,628,726 | A |   | 5/1997  | Cotter |
| 5,762,646 | A | * | 6/1998  | Cotter ......................... 604/410 |
| 5,845,943 | A | * | 12/1998 | Ramacier et al. ............. 285/12 |
| 5,868,433 | A |   | 2/1999  | Matkovich |

* cited by examiner

*Primary Examiner*—Catherine S. Williams
(74) *Attorney, Agent, or Firm*—Stephen R. Greiner

(57) ABSTRACT

A releasable tubing connector including a male part that can be selectively fastened to a female part. The male and female parts are provided with internal valve assemblies that cooperate with one another to permit fluid to flow through the tubing connector. When the male and female parts are fastened together, fluid can flow through the releasable tubing connector. On the other hand, when the male and female parts are unfastened, fluid can flow through neither.

6 Claims, 2 Drawing Sheets

RELEASABLE TUBING CONNECTOR

FIELD OF THE INVENTION

The present invention relates generally to surgical apparatus and, more particularly, to aseptic connectors or couplings.

BACKGROUND OF THE INVENTION

Individuals undergoing medical treatments in hospital settings frequently find themselves connected to catheters which are tubular surgical instruments for withdrawing fluids from a cavity in the body. In normal use, one end of a catheter is introduced into the bladder through the urethra for withdrawing urine and the other end is connected to a bag or bottle for collecting the withdrawn urine. Despite their widespread use and great utility, catheters limit the mobility of a user, tethering him to a fluid collector. Over long periods of time, such a loss of mobility can lead to depression and other medical problems.

Products have been proposed that permit catheters and other tubular surgical instruments to be parted. Many of these products utilize small components or portions that are rotated relative to one another. Unfortunately, many infirm or elderly individuals cannot manipulate these things and, hence, find them to be useless. A need, therefore, exists for a releasable tubing connector that can be readily operated by one of limited strength or muscular dexterity to separate the end of a catheter inserted into the operator from the end connected to a fluid collector so that the operator can travel away from the fluid collector from time to time without assistance.

SUMMARY OF THE INVENTION

In light of the problems associated with the known products for connecting tubular surgical instruments, it is a principal object of the invention to provide a releasable tubing connector that can be easily operated by virtually anyone. The connector can be used to connect and disconnect two lengths of tubing without resort to additional tools and long periods of training.

It is another object of the present invention to provide a tubing connector of the type described that prevents fluids from siphoning from two lengths of tubing when such are disconnected from one another. Similarly, fluids, such as air, are prevented by the tubing connector from entering into two lengths of tubing when such are disconnected from one another.

It is an object of the invention to provide improved elements and arrangements thereof in a tubing connector for the purposes described which is lightweight in construction, inexpensive to manufacture, and fully dependable in use.

Briefly, the tubing connector in accordance with this invention achieves the intended objects by featuring including male and female parts that can be selectively fastened to one another and include internal valve assemblies that cooperate with one another to selectively permit fluid to flow through the connector. The male part includes a plug, a first tubing insert, and a first fluid flow passageway extending between the plug and first tubing insert. The female part, however, includes a socket portion, a second tubing insert, and a second fluid flow passageway extending between the socket portion and second tubing insert. The second fluid flow passageway is configured to receive the plug. A locking key is slidably secured to the socket portion so as to cross the second passageway. The locking key has an opening of sufficient size to permit the passage of the plug into the second passageway so that the locking key can enter the peripheral groove. The locking key also has a tapered slot adjacent the opening. A spring-biased pin is secured to the second tubular body and has a tapered shaft positioned within the tapered slot. A first end of the tapered shaft has a width sufficient to wedge against the locking key and retain the locking key outside the peripheral groove. A second end of the tapered shaft has a width that is relatively narrower than that of the first end thereby permitting the locking key to enter the peripheral groove when the second end is positioned in the tapered slot. A spring is secured to the second tubular body for urging the locking key into the peripheral groove.

The foregoing and other objects, features and advantages of the present invention will become readily apparent upon further review of the following detailed description of the preferred embodiment as illustrated in the accompanying drawings.

BRIEF DESCRIPTION OF THE DRAWINGS

The present invention may be more readily described with reference to the accompanying drawings, in which.

Similar reference characters denote corresponding features consistently throughout the accompanying drawings.

DETAILED DESCRIPTION OF THE PREFERRED EMBODIMENT

Figure 1:
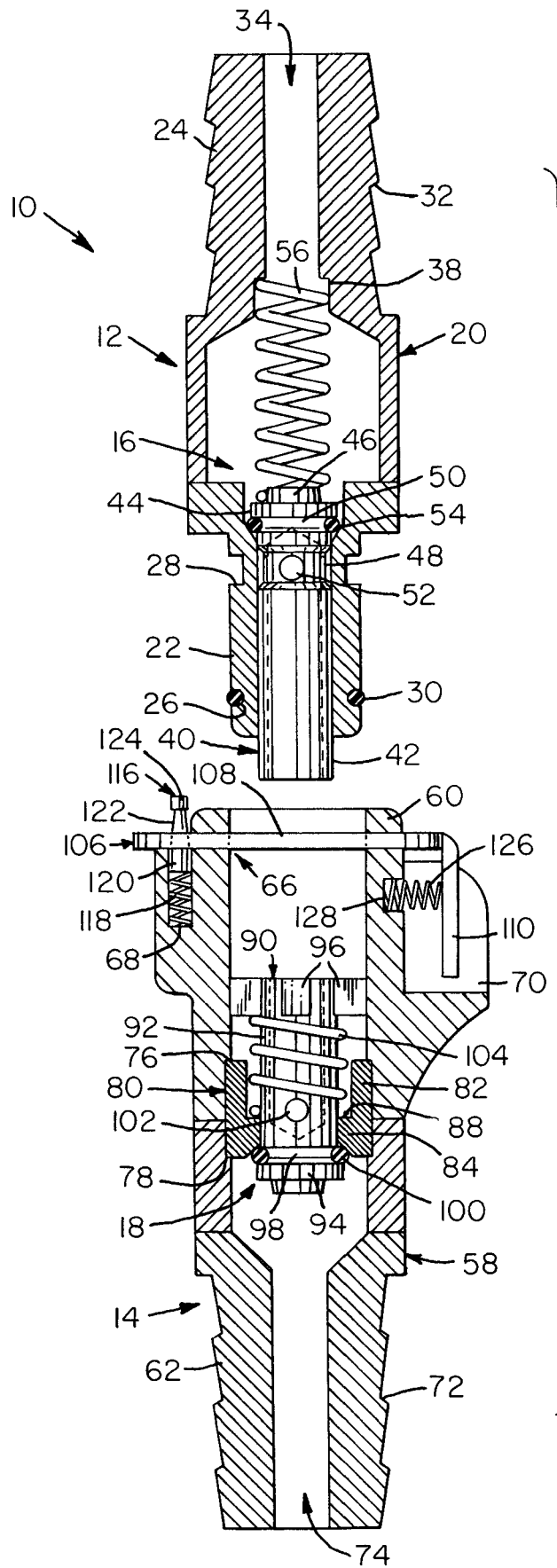
FIG. 1 is a longitudinal cross-sectional view of a releasable tubing connector in accordance with the present invention having its male and female parts uncoupled.

Referring now to the FIGS., a tubing connector in accordance with the present invention is shown at 10. Tubing connector 10 has a male part 12 that can be selectively fastened to a female part 14. Parts 12 and 14 are provided with internal valve assemblies 16 and 18 that cooperate with one another to permit fluid to flow through tubing connector 10.

Part 12 comprises a tubular body 20 having a plug 22 and a tubing insert 24 joined together at their inner ends. Preferably, plug 22 is cylindrical in form and has peripheral grooves 26 and 28 at its inner and outer ends. Peripheral groove 26 carries an O-ring 30. Tubing insert 24 is also cylindrical and has a plurality of side-by-side grooves 32 with sloping floors that serve to secure part 12 to a length of tubing (not shown).

Plug 22 and tubing insert 24 are hollow and define a passageway 34 extending from one end of tubular body 20 to the other. Passageway 34 can be seen to be enlarged somewhat at the inner end of plug 22 so as to provide part 12 with a valve seat 36. Similarly, passageway 34 is enlarged at the inner end of tubing insert 24 so as to provide part 12 with a spring seat 38.

A hollow stem 40 is positioned within passageway 34 and extends from one end of plug 22 to the other end thereof. Stem 40 includes a tube 42 with an enlarged cap 44 affixed to its inner end. A spring-retaining stud 46 projects from the inner end of cap 44.

Peripheral grooves 48 and 50 are provided in tube 42 and cap 44. Groove 48 includes a plurality of openings 52 at its base that offer fluid communication between the interior and exterior of tube 42. Groove 50, on the other hand, carries an O-ring 54 that engages valve seat 36 so as to prevent fluid from flowing through part 12.

A compressed spring 56 is positioned within passageway 34. One end of the spring 56 is fitted within spring seat 38 of tubing insert 24 and the other end of spring 56 is fitted about retaining stud 46 on stem 40. Spring 56 normally biases O-ring 54 into engagement with valve seat 36 and retains the outer end of stem 40 in a position where it extends from plug 22.

Part 14 comprises a tubular body 58 having a socket portion 60 and a tubing insert 62 joined at their inner ends by an intermediate portion 64. Socket portion 60 is generally cylindrical in form and includes a transverse slot 66 in its outer end. A minor bore 68 is provided in socket portion 60 at one end of slot 66 and a relatively wide recess 70 is provided in socket portion 60 at the other end of slot 66. Tubing insert 62, however, is cylindrical and has a plurality of side-by-side grooves 72 with sloping floors that serve to secure part 14 to a length of tubing (not shown).

Socket portion 60, intermediate portion 64 and tubing insert 62 are hollow and define a passageway 74 extending from one end of tubular body 58 to the other. Passageway 74 is provided with a large diameter at one end of tubular body 58 to receive plug 22 and is provided with a small diameter at the other end of tubular body 58 for easy insertion into a length of tubing. Passageway 74 is enlarged somewhat at the inner ends of socket and intermediate portions 60 and 64 so as to provide shoulders 76 and 78 that serve as stops to retain a sealing portion 80.

Sealing portion 80 comprises a ring 82 sized to fit snugly against socket and intermediate portions 60 and 64 between shoulders 76 and 78. Ring 82 has an inwardly extending, annular flange 84 at one end thereof. The side of flange 84 proximate tubing insert 62 defines a valve seat 86 whereas the side of flange 84 proximate socket portion 60 defines a spring seat 88.

A piston 90 slidably extends through sealing portion 80. Piston 90 includes a tube 92 with an enlarged cap 94 affixed to its inner end and a plurality of fins 96 extending radially outward from its outer end. Fins 96 slidably engage the inner surface of socket portion 60 and help center piston 90 in passageway 74.

Figure 2:
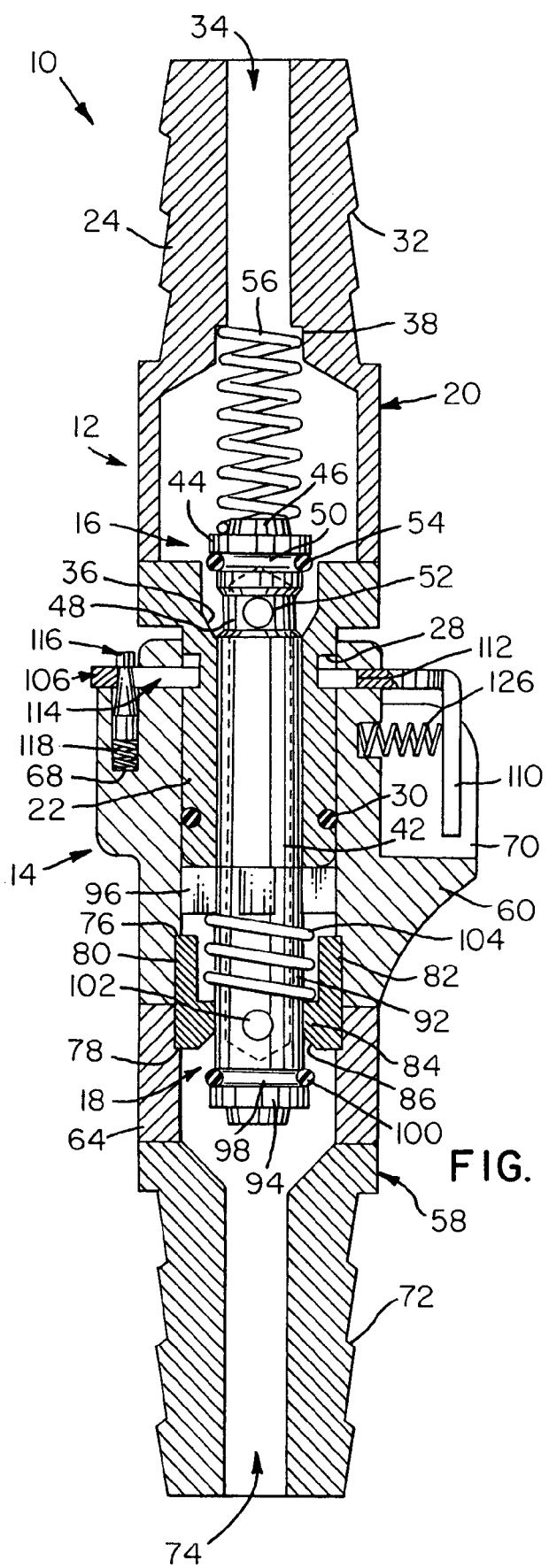
FIG. 2 is a longitudinal cross-sectional view of the tubing connector of FIG. 1 having its male and female parts coupled together.

A peripheral groove 98 is provided in tube 92 on the outer side of cap 94 to carry an O-ring 100 that engages valve seat 86 of sealing portion 80 to prevent fluid from flowing through part 14. Positioned between groove 98 and fins 96 is an opening 102 that offers fluid communication between the interior and exterior of tube 92. When parts 12 and 14 are uncoupled, a shown in FIG. 1, opening 102 is positioned on the inner side of flange 84 thereby preventing fluid from passing through part 14. Nonetheless, when parts 12 and 14 are coupled, as shown in FIG. 2, opening 102 is positioned by the motion of piston 90 on the outer side of flange 84 thereby permitting fluid to flow through part 14.

A compressed spring 104 is positioned within passageway 74 and about tube 92. One end of spring 104 presses against spring seat 88 and the other end of spring 104 presses against fins 96 of piston 90. Spring 104 normally biases O-ring 100 into engagement with valve seat 86 and retains the outer end of piston 90 in a position where it can be engaged by plug 22 when such is inserted into passageway 74.

A locking key 106 is slidably secured to socket portion 60. As shown, key 106 includes a retaining plate 108 slidably positioned within slot 66. A pushing plate 110 is secured at right angles to the bottom of retaining plate 108 and extends into recess 70.

Retaining plate 108 includes an opening 112 normally held in axial alignment with passageway 74 and has a diameter that is slightly larger than that of plug 22. Extending from opening 112 is a tapered slot 114 that is in alignment with bore 68. As shown, the length of slot 114 is sufficient to extend past bore 68 and the width of slot 114 decreases linearly moving away from opening 112.

Figure 3:
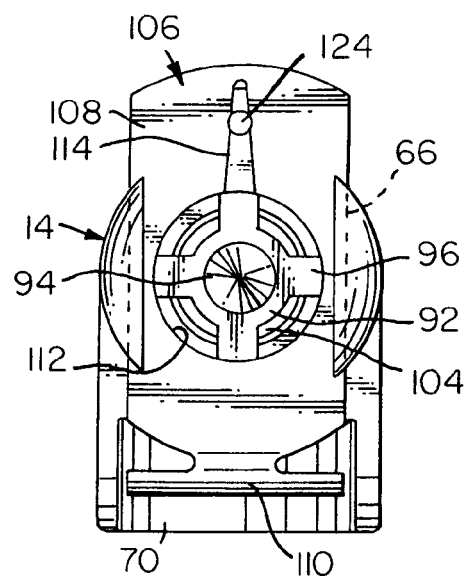
FIG. 3 is a front view of the female part of the tubing connector.

Positioned within bore 68 is a retaining pin 116 and a compressed spring 118 that urges pin 116 outwardly from bore 68. Pin 116 includes a base 120 that engages spring 118 and has a width that is greater than that of slot 114 at all points along the length of slot 114. A tapered shaft 122 extends from base 120 and through slot 114. Shaft 122 has a width at its narrowed outer end that is substantially the same as the width of slot 114 at its narrowed outer end and a width at its wide inner end that corresponds with that of slot 114 at the point where opening 112 and passageway 74 are in axial alignment as shown in FIGS. 1 and 3. An enlarged head 124 is secured to the outer end of shaft 122 to serve as a pushbutton.

A compressed spring 126 extends from a bore 128 at the base of recess 70 and engages pushing plate 110. Spring 126 maintains constant pressure on pushing plate 110 that tends to pull opening 112 in retaining plate 108 into misalignment with passageway 74. From the foregoing, it should be appreciated that when pin 116 is fully extended from bore 68 and into slot 114, plug 22 can be selectively inserted into socket portion 60. By depressing pin 116 into bore 68 against the light force of spring 118 when plug 22 is fully inserted into socket portion 60, retaining plate 108 is pulled into groove 28 so as to selectively lock parts 12 and 14 together.

Use of connector 10 a straightforward. First, tubing inserts 24 and 62 of parts 12 and 14 are put in the ends of lengths of tubing that the user is desirous of connecting together. Next, plug 22 is pressed through opening 112 in locking key 106 and inserted fully into passageway 74 in tubular body 58 to open the internal valve assemblies 16 and 18. Valve assemblies 16 and 18 open as stem 40 presses against piston 90 causing both to move inwardly and to unseat O-rings 54 and 100 from valve seats 36 and 86. Fluid may now move through parts 12 and 14 following a course through: passageway 34, openings 52, tube 42, tube 92, openings 102 and passageway 74.

Parts 12 and 14 can be locked together. By pressing head 124 of retaining pin 116, tapered shaft 122 is inserted into bore 68. Since the narrow outer end of shaft 122 cannot serve as a wedge in slot 114 to prevent movement of locking key 106 under the influence of compressed spring 126, retaining plate 108 is pushed into groove 28 in tubular body 20. With plate 108 into groove 28, plug 22 cannot be withdrawn from tubular body 58.

Parts 12 and 14 are released from one another simply by pressing plate 110 into recess is 70. Movement of plate 110 results in corresponding movement of plate 108 which brings opening 112 into alignment with passageway 74 thereby freeing plug 22. Simultaneously, spring 118 drives the wide portion of tapered shaft 122 adjacent base 120 of retaining pin 116 into slot 114. With shaft 122 serving as a wedge against the movement of key 106, plate 108 is prevented from reentering groove 28. Plug 22 is now withdrawn from passageway 74, separating parts 12 and 14.

As parts 12 and 14 are separated, valve assemblies 16 and 18 return to their original and closed configurations under the influences of compressed springs 56 and 104. Fluid, thus, cannot flow from the lengths of tubing to which parts 12 and 14 are connected when parts 12 and 14 are separated from one another. Similarly, fluids such as air cannot pass through parts 12 and 14 to enter into the separated lengths of tubing to which such are connected.

While the invention has been described with a high degree of particularity, it will be appreciated by those skilled in the art that modifications may be made thereto. Therefore, it is to be understood that the present invention is not limited to the sole embodiment described above, but encompasses any and all embodiments within the scope of the following claims.

I claim:

1. A releasable tubing connector, comprising:
 a male part including a first tubular body having a plug with a peripheral groove at one end thereof and a first tubing insert at the other end thereof, said first tubular body also having a first fluid flow passageway extending through said plug and said first tubing insert; and,
 a female part including:
  a second tubular body having a socket portion at one end thereof and a second tubing insert at the other end thereof, said second tubular body also having a second fluid flow passageway extending through said socket portion and said second tubing insert, said second fluid flow passageway in said socket portion being adapted to receive said plug;
  a locking key being slidably secured to said socket portion so as to cross said second passageway, said locking key having an opening of sufficient size therein to permit the passage of said plug into said second passageway so that said locking key can enter said peripheral groove, said locking key also having a tapered slot adjacent said opening, and said slot having a length and a width that gradually and uniformly decreases along said length;
  a spring-biased pin secured to said second tubular body, said pin having a tapered shaft positioned within said tapered slot, a first end of said tapered shaft having a width sufficient to wedge against said locking key and retain said locking key outside said peripheral groove, a second end of said tapered shaft having a width that is relatively narrower than that of said first end thereby permitting said locking key to enter said peripheral groove when said second end is positioned in said tapered slot, and said tapered shaft gradually and uniformly decreasing in diameter from said first end to said second end; and,
  a spring secured to said second tubular body for urging said locking key into said peripheral groove.

2. The releasable tubing connector according to claim 1 wherein said male and female parts include internal valve assemblies that cooperate with one another to selectively permit fluid to flow through said tubing connector.

3. The releasable tubing connector according to claim 2 wherein said first fluid flow passageway includes opposed valve and spring seats and said internal valve assembly of said male part comprises:
 a hollow stem being positioned within said first fluid flow passageway and extending through said plug so as to normally project outwardly therefrom, said stem having a tube with an enlarged cap affixed to one end thereof, said tube having a peripheral groove with at least one opening therein offering fluid communication between the interior and exterior of said tube; and,
 a compressed spring is positioned within said first fluid flow passageway, one end of said compressed spring being fitted within said spring seat and the other end of compressed spring being secured to said enlarged cap so as to urge said enlarged cap toward said valve seat and urge said tube from said plug.

4. The releasable tubing connector according to claim 2 wherein said internal valve assembly of said female part comprises:
 a sealing portion being positioned within said second fluid flow passageway and having an inwardly extending, annular flange, one side of said flange defining a valve seat and the other side of said flange defining a spring seat;
 a piston slidably extending through said sealing portion, said piston having a tube with an enlarged cap affixed to one end thereof and a plurality of fins extending radially outward from the other end thereof, said fins slidably engaging said socket portion thereby centering said piston in said second fluid flow passageway, said tube having an opening between said enlarged cap and said fins; and,
 a compressed spring being positioned within said second fluid flow passageway and about said tube, one end of said compressed spring pressing against said spring seat and the other end of said the compressed spring pressing against said fins.

5. A releasable tubing connector, comprising:
 a male part and a female part being adapted for selectively attaching two lengths of tubing to one another, said male part being provided with a first internal valve assembly located within a first fluid flow passageway and said female part being provided with a second internal valve assembly located within a second fluid flow passageway, said first and second internal valve assemblies being adapted to engage one another to permit fluid to flow through said tubing connector; and wherein a locking key with a uniformly tapered slot along its length on either of the male part and female part can enter a peripheral groove on the other part and where a tapered spring biased pin is positioned in the uniformly tapered slot;
 said first internal valve assembly including:
  opposed, first, valve and spring seats in said first fluid flow passageway;
  a hollow stem normally projecting outwardly from said male part, said stem having a first tube with a first enlarged cap affixed to one end thereof, said first tube having a first peripheral groove with a first opening therein offering fluid communication between the interior and exterior of said first tube; and,
  a first compressed spring having one of its ends engaging said first spring seat and the other of its ends engaging said first enlarged cap so as to urge said first enlarged cap toward said first valve seat and urge said first tube from said male part;
 said second internal valve assembly including:
  an annular flange projecting into said second fluid flow passageway, one side of said flange defining a second valve seat and the other side of said flange defining a second spring seat;
  a piston slidably extending through said annular flange, said piston having a second tube with a second enlarged cap affixed to one end thereof and a plurality of fins extending radially outward from the other end thereof, said second tube having a second opening between said second enlarged cap and said fins; and, a second compressed spring being positioned about said second tube, one end of said second compressed spring engaging said spring seat and the other end of said second compressed spring engaging said fins;

whereby attaching said male part to said female part causes said hollow stem and said piston to engage one another and to displace one another such that said first enlarged cap disengages said first valve seat in said second enlarged cap disengages said second valve seat to permit fluid to flow through said first fluid flow passageway and said second fluid flow passageway.

6. A releasable tubing connector, comprising:

a male part including:
- a first tubular body having a plug with a peripheral groove at one end thereof and a first tubing insert at the other end thereof, said first tubular body also having a first fluid flow passageway extending through said plug and said first tubing insert, said first fluid flow passageway being configured to contain a first valve seat and a first spring seat located in opposition to said first valve seat;
- a hollow stem projecting from said plug, said stem having a first tube with a first enlarged cap affixed to one end thereof, said first tube having a first peripheral groove with a first opening therein offering fluid communication between the interior and exterior of said first tube; and,
- a first compressed spring having one of its ends engaging said first spring seat and the other of its ends engaging said first enlarged cap so as to urge said first enlarged cap toward said first valve seat and to urge said first tube from said plug; and, a female part including:
- a second tubular body having a socket portion at one end thereof and a second tubing insert at the other end thereof, said second tubular body also having a second fluid flow passageway extending through said socket portion and said second tubing insert, said second fluid flow passageway in said socket portion being adapted to receive said plug, said second fluid flow passageway also having an annular flange, one side of said annular flange defining a second valve seat and the other side of said flange defining a second spring seat;
- a locking key being slidably secured to said socket portion so as to cross said second passageway, said locking key having an opening of sufficient size therein to permit the passage of said plug into said second passageway so that said locking key can enter said peripheral groove, said locking key also having a uniformly tapered along it's length slot adjacent said opening;
- a spring-biased pin secured to said second tubular body, said pin having a tapered shaft positioned within said tapered slot, a first end of said tapered shaft having a width sufficient to wedge against said locking key and retain said locking key outside said peripheral groove, a second end of said tapered shaft having a width that is relatively narrower than that of said first end thereby permitting said locking key to enter said peripheral groove when said second end is positioned in said tapered slot;
- a piston slidably extending through said annular flange, said piston having a second tube with a second enlarged cap affixed to one end thereof and a plurality of fins extending radially outward from the other end thereof, said second tube having a second opening between said second enlarged cap and said fins; and,
- a second compressed spring being positioned about said second tube, one end of said second compressed spring engaging said spring seat and the other end of said second compressed spring engaging said fins;

whereby attaching said male part to said female part causes said hollow stem and said piston to engage one another and to displace one another such that said first enlarged cap disengages said first valve seat in said second enlarged cap disengages said second valve seat to permit fluid to flow through said first fluid flow passageway and said second fluid flow passageway.

* * * * *